(12) United States Patent
Teuscher et al.

(10) Patent No.: US 7,147,252 B2
(45) Date of Patent: Dec. 12, 2006

(54) MEDICAL CONNECTOR

(75) Inventors: L. John Teuscher, Springville, UT (US); D. Theron Van Hooser, Salt Lake City, UT (US); Edward B. Madsen, Riverton, UT (US); Chet M. Crump, Draper, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/037,443

(22) Filed: Dec. 21, 2001

(65) Prior Publication Data

US 2003/0116963 A1 Jun. 26, 2003

(51) Int. Cl.
*F16L 22/00* (2006.01)

(52) U.S. Cl. ............... 285/280; 285/134.1; 128/207.14

(58) Field of Classification Search ............. 285/134.1, 285/135.4, 276, 278, 281, 280, 275; 128/207.14
See application file for complete search history.

(56) References Cited

U.S. PATENT DOCUMENTS

| | | | | |
|---|---|---|---|---|
| 331,806 | A | * | 12/1885 | McGahan ................. 285/278 |
| 398,620 | A | * | 2/1889 | Jobes ..................... 285/114 |
| 708,104 | A | * | 9/1902 | Warner .................... 285/87 |
| 1,056,762 | A | * | 3/1913 | McGahan ................. 285/278 |
| 2,238,535 | A | * | 4/1941 | Meyer et al. ............. 285/281 |
| 2,379,035 | A | * | 6/1945 | Phillips ................... 210/448 |
| 2,531,021 | A | * | 11/1950 | Bard ...................... 285/276 |
| 2,833,568 | A | * | 5/1958 | Corsette .................. 285/281 |
| 3,473,832 | A | * | 10/1969 | Kreidel, Sr. et al. ....... 285/98 |
| 4,229,024 | A | * | 10/1980 | Oberrecht et al. ......... 285/98 |
| 4,272,108 | A | * | 6/1981 | Maasberg ................. 285/95 |
| 4,676,241 | A | | 6/1987 | Webb et al. |
| 4,774,940 | A | | 10/1988 | Linder |
| 5,176,415 | A | * | 1/1993 | Choksi .................... 285/331 |
| 5,263,478 | A | | 11/1993 | Davis |
| 5,355,876 | A | | 10/1994 | Brodsky et al. |
| 5,370,610 | A | | 12/1994 | Reynolds |
| 5,513,633 | A | | 5/1996 | Islava |
| 5,620,426 | A | | 4/1997 | Braithwaite |
| 5,642,726 | A | | 7/1997 | Owens et al. |
| 5,694,922 | A | | 12/1997 | Palmer |
| 5,730,123 | A | | 3/1998 | Lorenzen et al. |
| 5,735,271 | A | | 4/1998 | Lorenzen et al. |
| 5,772,255 | A | | 6/1998 | Osborne et al. |
| 5,820,614 | A | | 10/1998 | Erskine et al. |
| 5,830,195 | A | | 11/1998 | Peters et al. |

(Continued)

FOREIGN PATENT DOCUMENTS

GB 2167512 * 5/1986 ................. 285/276

(Continued)

OTHER PUBLICATIONS

U.S. Appl. No. 09/680,125, filed Oct. 5, 2000.

(Continued)

*Primary Examiner*—David Bochna
(74) *Attorney, Agent, or Firm*—Dority & Manning (57) ABSTRACT

A connector for a respiratory assembly is provided. The connector includes a body that has a first end and a second end. The body has a passage disposed therethrough from the first end to the second end to allow for transport of fluids and objects through the body. The passage changes direction approximately 120° between the first end and the second end. The first end includes a coupling that is configured to rotatably engage a first member of the respiratory assembly. The second end includes a coupling that is configured to rotatably engage a second member of the respiratory assembly.

5 Claims, 6 Drawing Sheets

U.S. PATENT DOCUMENTS

| | | |
|---|---|---|
| 5,855,230 A | 1/1999 | Guala et al. |
| 5,882,348 A | 3/1999 | Winterton et al. |
| 6,095,505 A | 8/2000 | Miller |
| 6,494,203 B1 * | 12/2002 | Palmer .................. 128/202.27 |

FOREIGN PATENT DOCUMENTS

GB 2181806 * 4/1987 ................. 285/281

OTHER PUBLICATIONS

Written Opinion for PCT/US02/31697, May 24, 2004.

IPER for PCT/US02/31697, Oct. 15, 2004.

* cited by examiner

PRIOR ART

FIG. 7

MEDICAL CONNECTOR

BACKGROUND

Endotracheal intubation is a common procedure in the field of respiratory medical care. Endotracheal intubation tubes are used in many situations for providing artificial airways for passage of respiratory gasses and medical procedure devices to patients. For instance, endotracheal tubes may be used to insert a catheter therethrough in order to clean lung secretions from a patient. Endotracheal tubes may be used in situations where patients have stopped independent breathing and are required to be supported on a ventilator. In addition, endotracheal tubing may be used for other procedures such as: oxygenation of the lungs; elimination or reduction of residual carbon dioxide from the lungs; visual inspection of portions of the respiratory system; sampling sputum and gasses; measuring parameters such as flow rates, pressure, and temperature of gasses within the respiratory system; and/or the administration of medication, gasses, and/or lavage.

Some respiratory circuits may include a humidifier. Humidifiers are important because breathing gasses supplied to a patient must be warm and humidified in order to provide quality inhalation therapy. Additionally, the use of humidifiers in a respiratory circuit is particularly important when patients are connected to a ventilator for lengthy amounts of time. Typically, a ventilator supplies air to a humidifier which then moisturizes and warms the air. This warm and humid air is then supplied via an endotracheal tube to the patient. The endotracheal tube is usually connected to a "Y" connector. Alternatively, the "Y" connector may be attached to a mask proximate to a patient's mouth. "Y" tubes are therefore used in applications that employ masks and those that employ endotracheal tubing. While one fork of the "Y" connector is supplied with breathing gas from the humidifier, the other fork of the "Y" connector typically provides an exhalation passageway for removing air from the patient.

It is often the case that a patient who is connected to such a circuit for prolonged periods of time will experience discomfort when the patient moves and pulls on the various tubing. One solution to this problem is the use of flexible tubing, however in many applications the use of flexible tubing is either not possible or impractical. For instance, it could be possible that medical tubing that is flexible enough will crimp and prevent the flow of air through the tubing. As such, many respiratory circuits employ moderate to rigid plastic tubing in construction of the endotracheal tubes and other components in the respiratory circuit.

U.S. Pat. No. 5,694,922 assigned to Ballard Medical Products shows a medical connector with hermetic seals. These hermetic seals are useful in eliminating patient discomfort because they allow for the respiratory circuit to move and swivel in response to a patient's movements, hence reducing the force transmitted to a patient during such movement. U.S. Pat. No. 5,694,922 is hereby incorporated by reference in its entirety for all purposes.

The present invention is an improvement upon connectors of the type that are used in a respiratory circuit.

SUMMARY

Objects and advantages of the invention will be set forth in part in the following description, or may be obvious from the description, or may be learned through practice of the invention.

The present invention provides for a connector for use on a respiratory assembly. The connector has a body that has a first end and a second end. The body has a passage disposed therethrough from the first end to the second end. The passage allows for the transport of fluids and objects through the body. In one embodiment, the passage changes direction approximately 120° between the first end and the second end. The first end includes a coupling that is configured to rotatably engage a first member of the respiratory assembly. Also, the second end includes a coupling that is configured to rotatably engage a second member of the respiratory assembly.

The present invention also encompasses a connector for a respiratory assembly as discussed immediately above where the first member is a tracheal tube and the second member is a ventilating tube.

Also included in the present invention is a connector for a respiratory assembly that has a first section that is substantially cylindrical in shape and has a first axis. The first section also has a first passage therethrough that allows for the transport of fluids and objects through the first section. The first section is rotatably engageable with a first member of the respiratory assembly. Also, a second section is included that is substantially cylindrical in shape. The second section is connected to the first section and has a second axis. The second section has a second passage therethrough, in communication with the first passage, that allows for the transport of fluids and objects through the second section. The second section is rotatably engageable with a second member of the respiratory assembly. Additionally, an angle of less than 180° and greater than 90° exists between the first axis and the second axis.

Alternatively, the present invention includes an exemplary embodiment as immediately discussed where the angle is about 120°.

Further included in the present invention is a connector for a respiratory assembly as previously discussed where the first member is a tracheal tube and the second member is a ventilating tube.

Also included in the present invention is a connector for a respiratory assembly that has a body with both a first end and a second end. The body has a passageway for the transport of fluids and objects therethrough. The body has a bend between the first end and the second end that is between about 100° and 150°. A first female bell housing is connected to the first end and has a first annular rib. Also, a second female bell housing is connected to the second end and has a second annular rib. A first sleeve is disposed within the first female bell housing. The first sleeve has a first annular sealing member that is configured to engage the first annular rib. This engagement creates a hermetic seal between the passageway and the outside of the respiratory assembly. Further, a second sleeve is disposed within the second female bell housing. The second sleeve has a second annular sealing member that is configured to engage the second annular rib. This engagement causes a hermetic seal between the passageway and the outside of the respiratory assembly. The first sleeve is adapted to engage a first member of the respiratory assembly, and permits rotational motion between the body and the first member of respiratory assembly. Also, the second sleeve is adapted to engage a second member of the respiratory assembly, and permit rotational motion between the body and the second member of the respiratory assembly.

BRIEF DESCRIPTION OF THE DRAWINGS

An embodiment of the present invention is described by way of example with reference to the accompanying drawings, in which.

DETAILED DESCRIPTION

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

Figure 1:
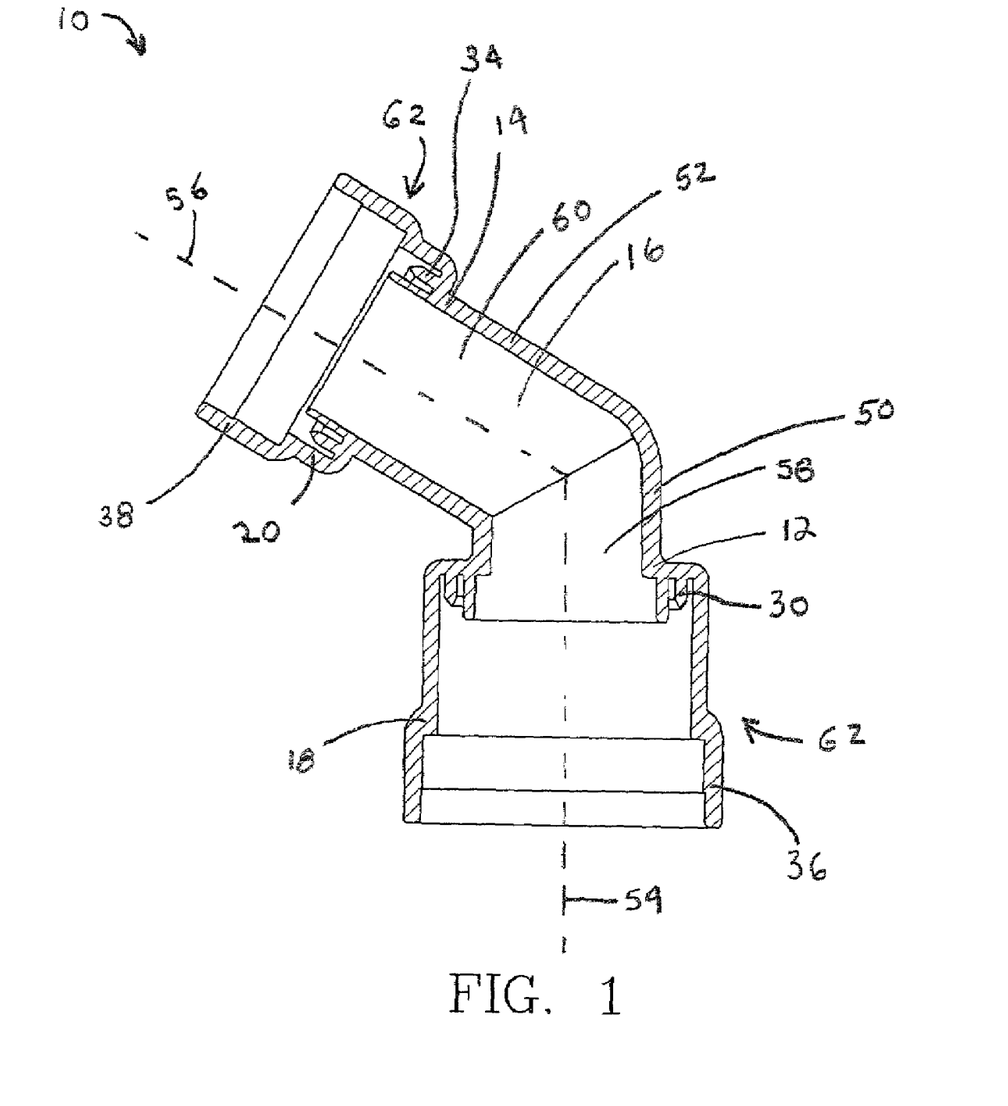
FIG. 1 is a cross-sectional view of an exemplary embodiment of a medical connector in accordance with the present invention. The drawing shows the medical connector having a bell housing on either end.

Referring now to the drawings, FIG. 1 shows an exemplary embodiment of a connector 10 in accordance with the present invention. The connector 10 is shown including a first section 50 and a second section 52. A first end 12 and a second end 14 are present which form the body of the connector 10. A passage 16 is present from the first end 12 to the second end 14 and allows for the transport of medical devices and fluids through the connector 10.

Couplings 62 are included on both the first end 12 and the second end 14. The couplings 62 are provided in order to allow for the connection of the connector 10 to tubes and devices of a respiratory circuit (not shown). As shown in FIG. 1, the couplings 62 are designed as a first end female bell housing 18 and a second end female bell housing 20. The two bell housings 18 and 20 are sized differently in order to engage different sized tubes of the respiratory circuit. Once connected, medical devices and fluids may be transported through the passage 16 from one of the tubes to the other. The passage 16 is made of a first passage 58 that goes through the first end 12 and a second passage 60 which goes through the second end 14. The two passages 58 and 60 intersect one another within the connector 10.

The first passage 58 has a first axis therethrough, and the second passage 60 has a second axis 56 therethrough. An angle greater than 90° and less than about 180° is formed between the first axis 54 and the second axis 56. This angle may be in the range of about 100° to about 150°. In one desirable embodiment, the angle is about 120°. This results in a connector 10 that has a bend of about 120° through its length. However, it is to be understood that other exemplary embodiments of the present invention exist where the angle between the first axis 54 and the second axis 56 is other than 120°.

Although the angle may be greater or less than 120°, an angle of 120° allows for a higher degree of patient comfort when the connector 10 is incorporated into a respiratory circuit. Additionally, an angle of about 120° allows for a greater ease of use for the medical caregiver when the connector 10 is incorporated into a respiratory circuit. In one exemplary embodiment of the present invention, the connector 10 may be attached to the ventilator circuit of a patient's endotracheal tube. In another exemplary embodiment, the connector 10 is attached to a tracheal tube and a humidifier tube of a respiratory circuit (not shown). Additionally, the connector 10 can be connected to other components of the respiratory circuit, and the present invention is not limited to an exemplary embodiment where the connector 10 is attached to a specific tube, instrument, or device.

Figure 2:
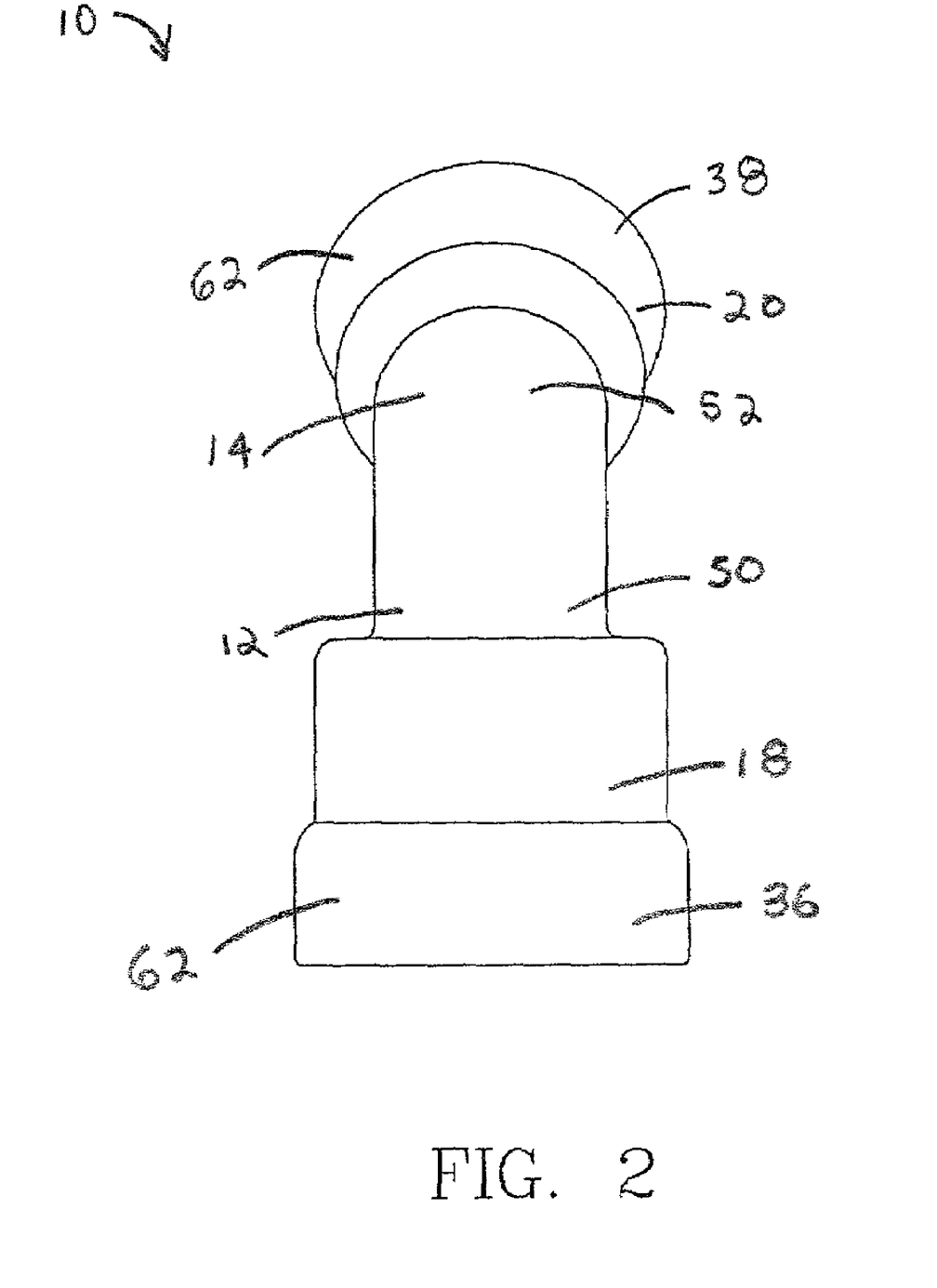
FIG. 2 is a front elevational view of the exemplary embodiment of a medical connector shown in FIG. 1.
Figure 3:
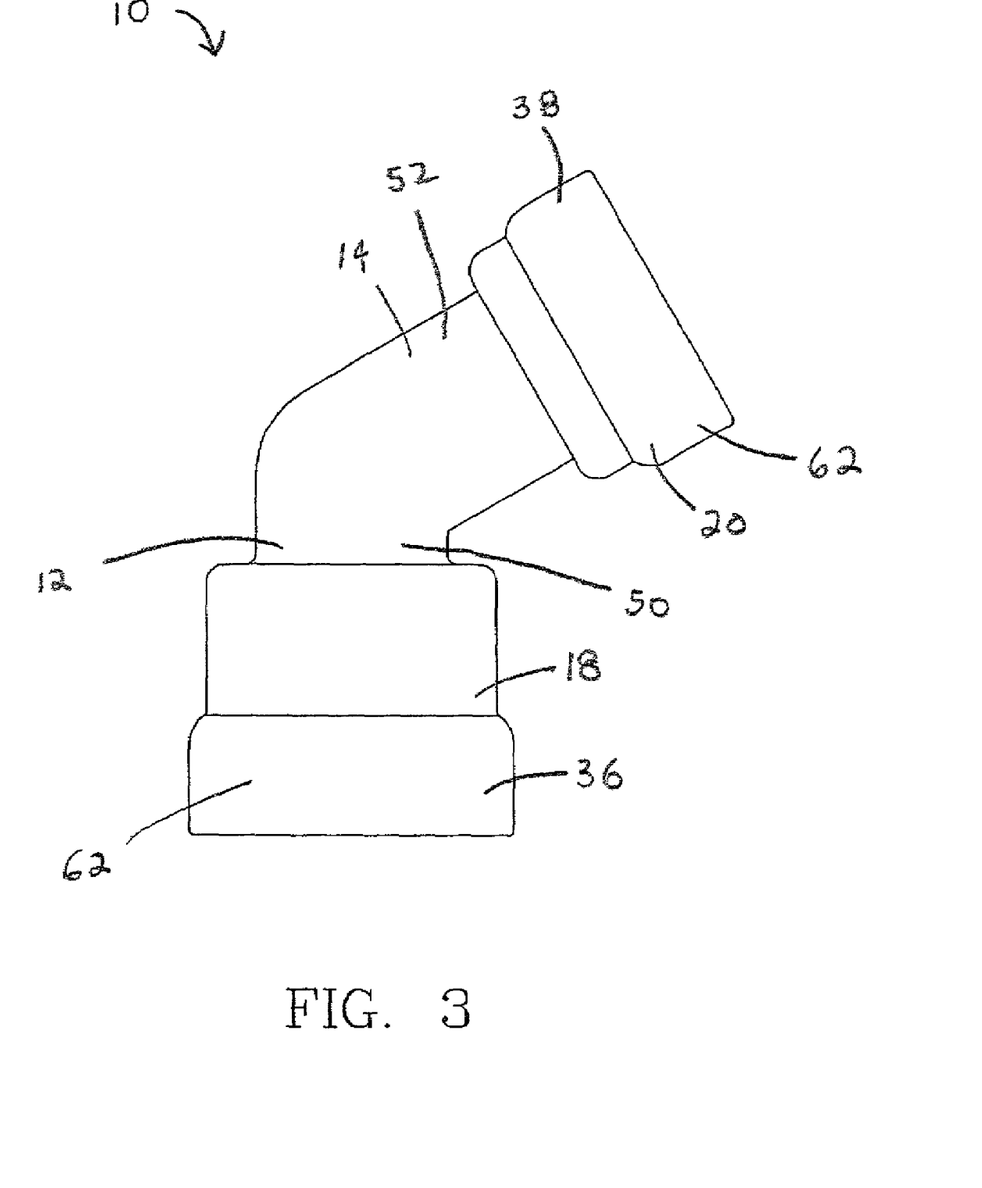
FIG. 3 is a side elevational view of the exemplary embodiment of a medical connector shown in FIG. 1.

FIGS. 2 and 3 show a front and side view respectively of an exemplary embodiment of a connector 10 in accordance with the present invention. The angle between the first end 12 and the second end 14 is about 120°. The connector 10 may be in one exemplary embodiment made of plastic and may be formed by injection molding. Additionally, in an another exemplary embodiment of the present invention, the connector 10, being a 120° elbow, may be incorporated into a patient end humidifier breathing circuit that is configured for use with a patient.

Figure 4:
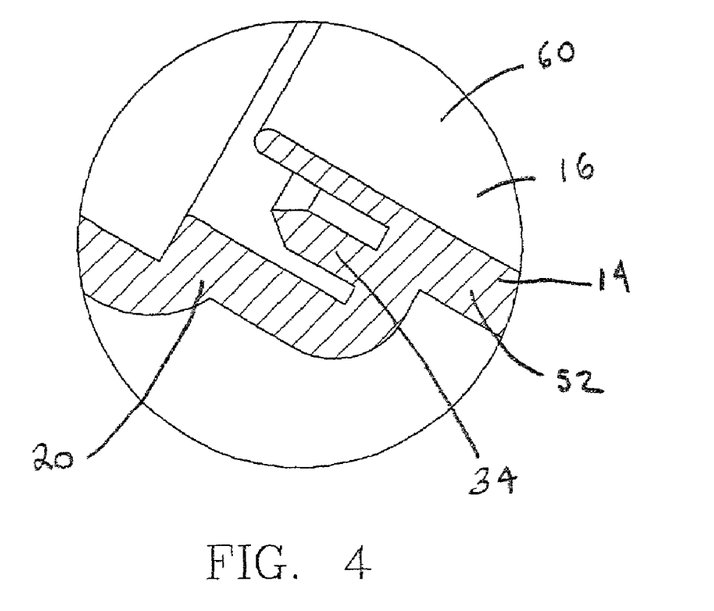
FIG. 4 is a detailed cross-sectional view of a second end female bell housing shown in FIG. 1. The drawing shows a second annular rib disposed within the second end female bell housing.
Figure 5:
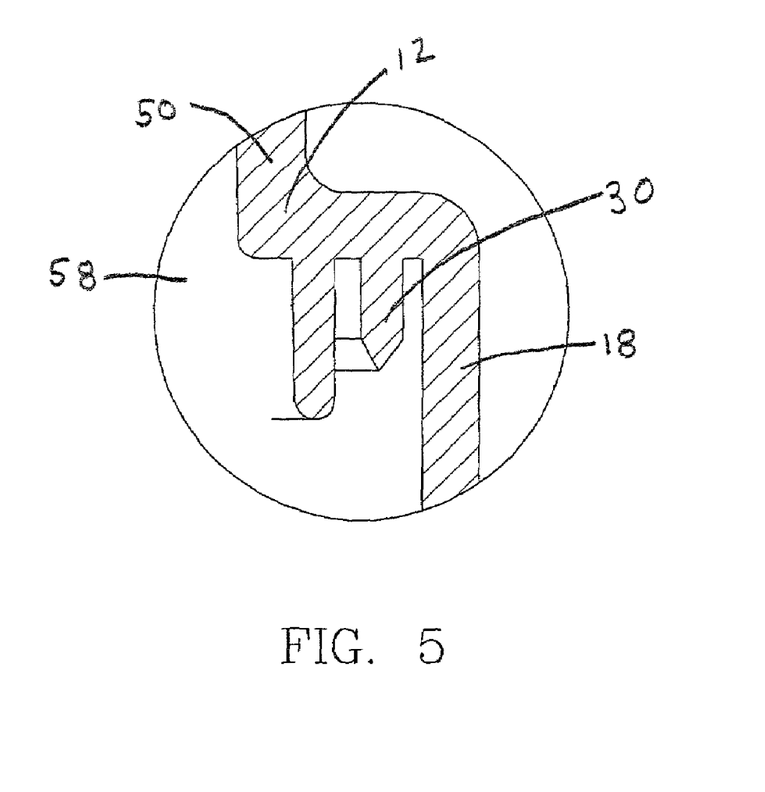
FIG. 5 is a detailed cross-sectional view of a first end female bell housing shown in FIG. 1. The drawing shows a first annular rib being disposed within the first end female bell housing.

FIG. 4 shows a detailed cross-sectional view of the second end female bell housing 20 of FIG. 1. Here, the second end 14 is shown as having a second annular rib 34 being disposed about the circumference of the second passage 60. However, it is to be understood that in other exemplary embodiments of the present invention, the second annular rib 34 may be placed in different locations. FIG. 5 shows a first annular rib 30 being disposed about the first passage 58 through the first end 12. The first annular rib 30 is similar to the second annular rib 34 shown in FIG. 4, and operates in the same manner. The operation of the annular ribs 30 and 34 will be discussed below.

An exemplary embodiment of the present invention provides for a connector 10 that has a first end 12 and a second end 14 that are both provided with couplings 62 that have a swivel fitting in order to allow for the connector 10 to swivel with respect to the tubes that are connected to the connector 10. Provision of a swivel fitting on the ends 12 and 14 of connector 10 are advantageous in that they minimize patient discomfort, increase the efficiency of the respiratory circuit, and help to prevent the blockage of the flow passageways through the respiratory circuit. However, the incorporation of swivel fittings necessitates the design of the fittings such that they are airtight and prevent leakage of fluids to and from the respiratory circuit and atmosphere. Such a design that provides for airtight swivel fittings is found in U.S. Pat. No. 5,694,922 which is assigned to the assignee of the present application and is incorporated herein in its entirety for all purposes.

Figure 6:
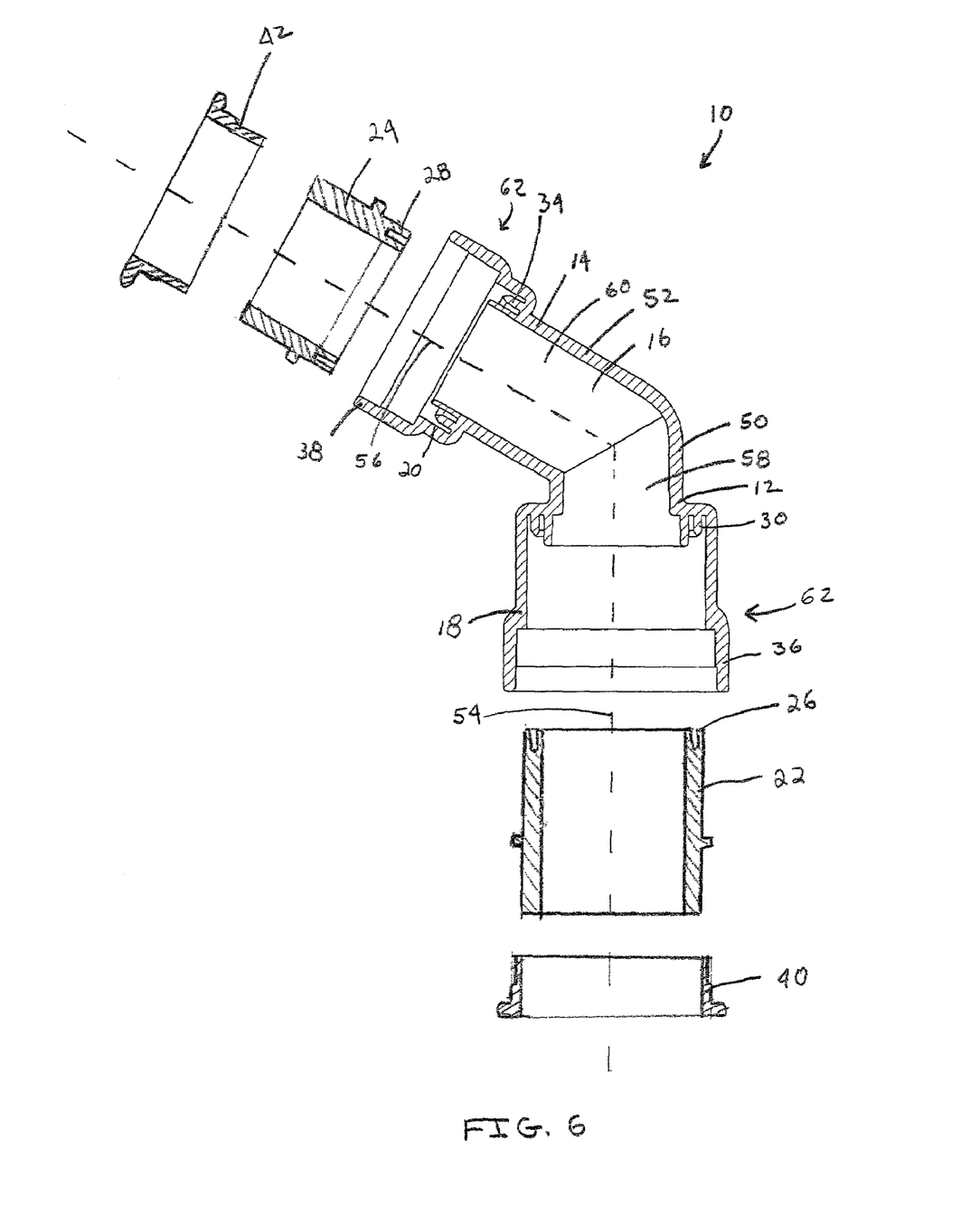
FIG. 6 is an exploded cross-sectional assembly view of an exemplary embodiment of a medical connector in accordance with the present invention. The drawing shows a first and second sleeve along with a first and second retainer that are to be inserted into the bell housings of the connector.

An exemplary embodiment of a connector 10 is shown in FIG. 6. Here, the first end 12 is provided with a first end female bell housing 18 that has a stepped annular ring 36. Additionally, the second end 14 is provided with a second end female bell housing 20 that has a stepped annular ring 38. The first end female bell housing 18 is designed in order to receive a first sleeve 22. The second end female bell housing 20 is designed to receive a second sleeve 24. A first retainer 40 may be slid over the first sleeve 22 and fitted within the stepped annular ring 36 of the first end female bell housing 18. Also, a second retainer 42 may be placed over the second sleeve 24 and fitted within the second end female bell housing 20 within the stepped annular ring 38. In one exemplary embodiment of the present invention, respiratory tubes may be attached to the first and second sleeves 22 and 24 in order to be rotatably attached to and in communication with one another through the connector 10. Additionally, another exemplary embodiment of the present invention includes a connector 10 where respiratory tubes are connected to the retainers 40 and 42 in order to be in communication and movable with respect to one another. The first and second retainers 40 and 42 therefore function as a bushing with flanges on the first and second sleeves 22 and 24 and rotatably engage the first and second stepped annular rings 36 and 38.

Figure 7:
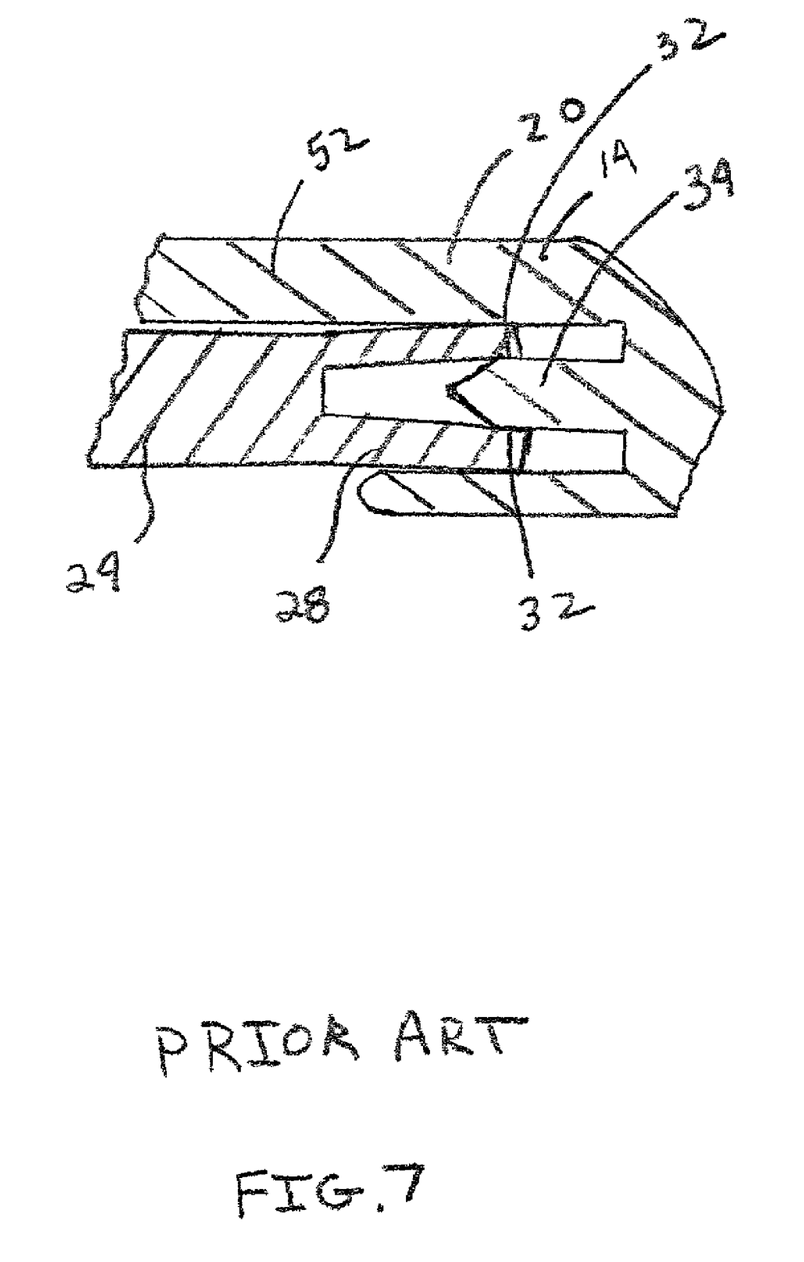
FIG. 7 is a cross-sectional detailed view of the second end female bell housing of FIG. 6. The drawing shows a second annular sealing member engaging a second annular rib to form a hermetic seal.

The first sleeve 22 is provided with a first annular sealing member 26 on one end thereof, and the second sleeve 24 is provided with a second annular sealing member 28 on one end thereof. FIG. 7 shows a detailed cross-sectional view of the second end female bell housing 20 in accordance with an exemplary embodiment of the present invention. The second end female bell housing 20 is shown as having the second annular rib 34 being formed thereon. Also, the second sleeve 24 is shown having the second annular sealing member 28 being a pair of projections with an intermittent slot. The second annular sealing member 28 is forced onto the second annular rib 34 in order to effect a pair of hermetic seals 32 within the second end female bell housing 20. Although shown as having two hermetic seals 32, it is to be understood that other exemplary embodiments of the present invention may include a connection that has only one hermetic seal 32 or several hermetic seals 32. The hermetic seal 32 prevents the passage of fluids between the inside of the respiratory circuit and the outside of the respiratory circuit. In effect, fluids are prevented from leaving the passage 16 and escaping to the atmosphere by way of the hermetic seals 32. The sealing arrangement also prevents contamination of the respiratory circuit.

Although shown as having first and second end female bell housings 18 and 20, it is to be understood that other exemplary embodiments of the present invention may include a connector 10 that has male housings with which to connect to tubes of the respiratory circuit. Additionally, other exemplary embodiments of the present invention exist where the couplings 62 are not swivel fittings, but are rigid connections between the connector 10 and the tubes and devices of the respiratory circuit. Here, the ends 12 and 14 are designed to rotate relative to the respiratory circuit by other means commonly known in the art. The connector 10 may be formed with couplings 62 such that the connector 10 is readily removable to and from the tubes and devices of the respiratory circuit. In addition, other exemplary embodiments of the present invention exist where the connector 10 is permanently bonded to the tubes and devices of the respiratory circuit. The connector 10 may be clear or opaque, and may be injection molded out of materials such as polycarbonate, acrylic, k-resin, ABS, or other suitable materials.

It should be understood that the invention includes various modifications that can be made to the exemplary embodiments of the medical connector described herein as come within the scope of the appended claims and their equivalents.

What is claimed is:

1. A connector for a respiratory assembly, comprising:
   a body having a first end defining a single opening and a second end defining a single opening, said body having a passageway for the transport of fluids and objects through said body, said body having about a 120° single constant bend between said first end and said second end, wherein the only access to said passageway is through said openings of said first and second ends;
   a first female bell housing connected to said first end having a first annular rib;
   a second female bell housing connected to said second end having a second annular rib;
   a first sleeve disposed within said first female bell housing, said first sleeve having a first annular sealing member configured to engage said first annular rib and effect a hermetic seal between said passageway and the outside of the respiratory assembly;
   a second sleeve disposed within said second female bell housing, said second sleeve having a second annular sealing member configured to engage said second annular rib and effect a hermetic seal between said passageway and the outside of the respiratory assembly;
   wherein said first sleeve is adapted to engage a first member of the respiratory assembly and permit rotational motion between said body and the first member of the respiratory assembly;
   wherein said second sleeve is adapted to engage a second member of the respiratory assembly and permit rotational motion between said body and the second member of the respiratory assembly; and
   wherein said passageway of said body extends through said first sleeve and said second sleeve such that said passage\way changing direction at a single constant angle of about 120° through the entire said first sleeve, the entire said second sleeve, and the entire said body.

2. The connector for a respiratory assembly of claim 1, wherein the first member is a tracheal tube and the second member is a ventilating tube.

3. The connector for a respiratory assembly of claim 1, wherein:
   said first and second ends each having a stepped annular ring; and
   further comprising a first and second retainer disposed in said respective annular rings for retaining said first and second sleeves in engagement with said respective first and second ends.

4. The connector for a respiratory assembly of claim 1, wherein said body, said first end, and said second end are plastic, are made by injection molding, and are substantially transparent.

5. The connector for a respiratory assembly of claim 1, wherein the first member is a tracheal tube and the second member is a humidifier tube.

* * * * *